United States Patent [19]
Akiba

[11] Patent Number: 5,891,014
[45] Date of Patent: Apr. 6, 1999

[54] PASSAGE STRUCTURE IN ENDOSCOPE AND ADAPTER USED WHEN WASHING PASSAGES IN ENDOSCOPE

[75] Inventor: Haruo Akiba, Omiya, Japan

[73] Assignee: Fuji Photo Optical Co., Ltd., Omiya, Japan

[21] Appl. No.: 114,572

[22] Filed: Jul. 13, 1998

[30] Foreign Application Priority Data

| Jul. 18, 1997 | [JP] | Japan | 9-210062 |
| Jul. 18, 1997 | [JP] | Japan | 9-210063 |
| Jul. 23, 1997 | [JP] | Japan | 9-214072 |

[51] Int. Cl.$^6$ .................................................. A61B 1/00
[52] U.S. Cl. ........................... 600/158; 600/159; 600/156
[58] Field of Search ................................. 600/104, 133, 600/143, 152, 153, 155, 156, 157, 158, 159

[56] References Cited

U.S. PATENT DOCUMENTS

| 3,903,387 | 9/1975 | Terada | 600/157 |
| 4,190,041 | 2/1980 | Chikama | 600/155 |
| 4,270,525 | 6/1981 | Furihata | 600/159 |
| 4,550,716 | 11/1985 | Kinoshita | 600/158 |
| 4,637,378 | 1/1987 | Sasa | 600/155 |
| 4,736,732 | 4/1988 | Shimonaka | 600/159 |
| 4,748,970 | 6/1988 | Nakajima | 60/158 |
| 4,765,312 | 8/1988 | Sasa | 600/158 |
| 4,779,624 | 10/1988 | Yokoi | 600/156 |
| 4,800,869 | 1/1989 | Nakajima | 600/158 |
| 5,386,817 | 2/1995 | Jones | 600/157 |
| 5,408,991 | 4/1995 | Iida | 600/155 |
| 5,447,148 | 9/1995 | Oneda | 600/158 |
| 5,674,183 | 10/1997 | Adachi | 600/156 |
| 5,697,888 | 12/1997 | Kobayashi | 600/157 |

*Primary Examiner*—John P. Leubecker
*Assistant Examiner*—Ira Hatton
*Attorney, Agent, or Firm*—Ronald R. Snider

[57] ABSTRACT

A passage structure of an endoscope which facilitates the passage washing operation by enabling all the passages to be washed with a washing brush passed through from the operating portion. A passage unit is removably attached to the operating portion, and the passages are exposed to a return portion provided at the rear end portion of the operating portion. The passage unit is provided with an auxiliary tube for, for example, flushing the lens surface, and an injection hole member having an injection hole and a replaceable check valve is removably connected thereto, thereby enabling washing of the tubes from the operating portion of the endoscope. A tight spring is fitted over a soft tube which is disposed in a straight line in the operating portion, and a tape is wound around the soft tube placed along a hard tube such as a suction tube. An adapter having a washing water injection hole is provided on the receiving portion of the operating portion which is connected to the passage unit, thereby facilitating a liquid chemical or the like to be injected to a fine tube.

8 Claims, 10 Drawing Sheets

PASSAGE STRUCTURE IN ENDOSCOPE AND ADAPTER USED WHEN WASHING PASSAGES IN ENDOSCOPE

BACKGROUND OF THE INVENTION

This application claims the priority of Japanese Patent Application No. 9-214072 filed on Jul. 23, 1997 and Application Nos. 9-210062 and 9-210063 filed on Jul. 18, 1997 which are incorporated herein by reference.

FIELD OF THE INVENTION

The present invention relates to a passage structure in an endoscope and an adapter used when washing passages in an endoscope which facilitate the washing and disinfection of air and water supply tubes, a suction tube, etc. provided within the endoscope.

DESCRIPTION OF THE RELATED ART

Electronic endoscopes are composed of an end portion having a CCD (Charged Coupled Device), an insertion portion, an operating portion and a cable. The cable connects the operating portion with a light source device and a processor for processing an image. By means of such an endoscope, it is possible to photograph and observe the internal structure of the body as an object of observation which is irradiated through a light guide. The endoscope is provided within with an air supply tube, a water supply tube, a suction tube, etc. through which air and water are supplied to an observation window or the like of the end portion, and contents within the body are sucked and discharged.

Since the endoscope is used for medical examination or treatment, it is necessary to wash and disinfect each passage. However, It is conventionally impossible to wash and disinfect the passages with efficiency. Although it is preferable to wash the passages with a brush, it is difficult to pass a washing brush from the end portion straight to the passage connector at the end portion of the cable. This is mainly because the endoscope as a whole is long; there is a largely curved portion in an internal passage, especially, within the operating portion; and when an mechanically operated valve is used as an air/water supply button or a suction button, a part of the passage becomes complicated (there is a disconnected portion) in that part, which makes it difficult to feed a washing brush to the depth.

It is therefore necessary to let washing water flow for a long time and a measure for improving the part of the operation valve so as to enable the washing brush to reach the farthest possible portion of a passage is adopted. Thus, the washing operation is troublesome, and each structure for facilitating the washing operation becomes complicated.

In addition, in a conventional endoscope, the water supply tube and the air supply tube are composed of a flexible tube except for the connecting portion or the like, so that during the washing of the interior of the tube, the passage is bent or warped inconveniently for washing. If the washing brush applies strong force to the tube, the flexible tube may sometimes slip out of the connecting portion or may even be broken.

SUMMARY OF THE INVENTION

Accordingly, it is a first object of the present invention to eliminate the above-described problems in the related art and to provide a passage structure of an endoscope which facilitates the passage washing operation by enabling all the passages to be washed with a washing brush passed through from the operating portion, while preventing a passage from being bent or warped by the insertion of the washing brush.

It is a second object of the present invention to provide an adapter used when washing passages in an endoscope which enables a liquid chemical to be easily injected into a plurality of fine tubes which are separated from each other in the middle of a passage.

To achieve the first object, in a first aspect of the present invention there is provided a passage structure of an endoscope, comprising: an operating portion which is provided therein with passages of the endoscope; a passage unit which is removably attached to the operating portion and which is provided with a passage for connecting the passages in the operating portion to an operating valve controller (solenoid valve unit and other supply or suction devices); a return portion for separating at least one of the passages so that the openings thereof are exposed to the outer peripheral portion of the operating portion, and forming a flow returning space at the exposed portions of the openings when the passage unit is mounted on the operating portion; an auxiliary passage provided in the operating portion in such a manner as to be connected to the passage unit; and an injection hole member removably attached to the passage unit and provided with a check valve which is replaceable when the injection hole member is removed from the passage unit.

The passage unit (duct unit) may be composed of a supporting portion formed of a highly heat-resistant synthetic resin material which can be subjected to heat disinfection (sterilization), and a flexible tube which is disposed from the supporting portion to the operating valve controller in such a manner as to be removably attached to connecting tubes of the supporting portion and the operating valve controller.

It is possible to make the passage unit disposable by composing it from a supporting portion of a synthetic resin material within which a passage is integrally formed, and a flexible tube connected to the supporting portion.

According to the passage structure provided in the first aspect of the present invention, since the openings of the separated passages are exposed to the return portion, it is possible to insert a washing brush from the openings so as to wash the passages. In addition, the auxiliary passage of the passage unit is utilized, for example, as a passage for injecting water to the observation window so as to flush the lens surface, or as a passage for supplying air, liquid or the like to the interior of the body as an object of observation. The injection hole member of the auxiliary passage is removable. It is therefore possible to subject the passage unit to washing and heat sterilization in the state in which the check valve is removed from the removed injection hole, and the flexible tube is removed from the connecting tube. If unused check valve and flexible tube are attached to the passage unit after the end of the washing and disinfection, it is usable as a new passage unit. In this case, the check valve and the flexible tube are used as disposable members (which are used only once and then thrown away).

It is also possible to make the passage unit as a whole disposable by forming the supporting portion of an inexpensive synthetic resin material and forming a flexible tube integrally therewith. In this case, the washing and disinfection of the passage unit is unnecessary.

In a second aspect of the present invention there is provided a passage structure of an endoscope, comprising: an operating portion which is provided therein with passages of the endoscope; a passage unit which is removably attached to the operating portion and which is provided with a passage for connecting the passages in the operating portion to an operating valve controller; and a return portion for separating at least one of the passages so that the openings thereof are exposed to the outer peripheral portion of the operating portion, and forming a flow returning space at the exposed portions of the openings when the passage unit is mounted on the operating portion; wherein when the passages include a soft tube disposed in a straight line, a tight spring is fitted over the soft tube.

It is possible to dispose a hard tube such as a suction tube in the endoscope, and bundle the hard tube and a soft tube such as an air supply tube or a water supply tube with an armoring member in a state in which the soft tube is placed along the hard tube.

According to the passage structure provided in the second aspect of the present invention, owing to the tight spring, the soft tube is firmly kept in a straight line and it is prevented from being bent even if a washing brush is inserted thereinto. In addition, when the soft tube is drawn close to the hard tube and they are bundled with an armoring member such as a tape, it is possible to prevent the soft tube in a straight line from being bent or warped. In this case, the armoring member serves as a fixing member for the soft tube.

In order to achieve the second object, in a third aspect of the present invention, there is provided an adapter used when washing passages (when injecting washing water into passages) in an endoscope which is provided with a main body having a first coupling portion where the openings of the passages are disposed and a passage unit having a second coupling portion to be coupled with the first coupling portion and maintaining the passage function, the adapter comprising: a third coupling portion which is coupled with the first coupling portion in such a manner that the space communicating with the openings of the passages is in an airtight state; and a washing water injection hole which is connected to the space communicating with the opening of the passage.

It is possible to dispose the openings of a suction tube, an air supply tube and a water supply tube at the first coupling portion and supply washing water to all of these passages.

In the passage structure provided in the first aspect of the present invention, a passage in the endoscope is separated in the operating portion and the openings of the separated fine tubes are exposed in order to wash and disinfect the endoscope with efficiency. However, when a liquid chemical such as a disinfectant is supplied from the exposed openings at the time of disinfection, it is sometimes difficult to supply the liquid chemical from a fine tube. When a liquid chemical is supplied from the exposed opening of a fine tube which is separated from another tube in the middle of a passage, an injecting device such as an injection syringe is generally utilized. It is, however, difficult to make the point of the injection device fine enough to be inserted into the fine tube, and the injecting operation is troublesome. Furthermore, since the diameters of the fine tubes are different from each other, it is inconveniently necessary to prepare an injecting device corresponding to each tube.

According to the adapter provided in the third aspect of the present invention, the first coupling portion and the second coupling portion which are, for example, screwed into each other are released from each other, the passage unit is removed from the operating portion, the third coupling portion is connected with the first coupling portion of the operating portion, and the adapter is attached thereto. If a liquid chemical (disinfectant) is injected from the injection hole of the adapter by an injection syringe or the like, disinfection using a liquid chemical is facilitated even if the tubes are fine or they have different diameters.

The above and other objects, features and advantages of the present invention will become clear from the following description of the preferred embodiments thereof, taken in conjunction with the accompanying drawings.

DESCRIPTION OF THE PREFERRED EMBODIMENT

First embodiment

Figure 4:
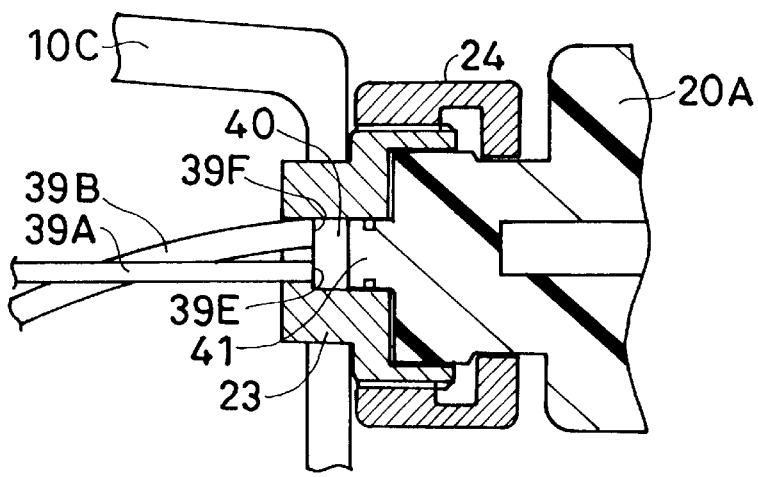
FIG. 4 shows the passage structure of the air supply tube in the first embodiment, which is a sectional view of FIGS. 2(A) and 2(B) taken along the line II—II.
Figure 5:
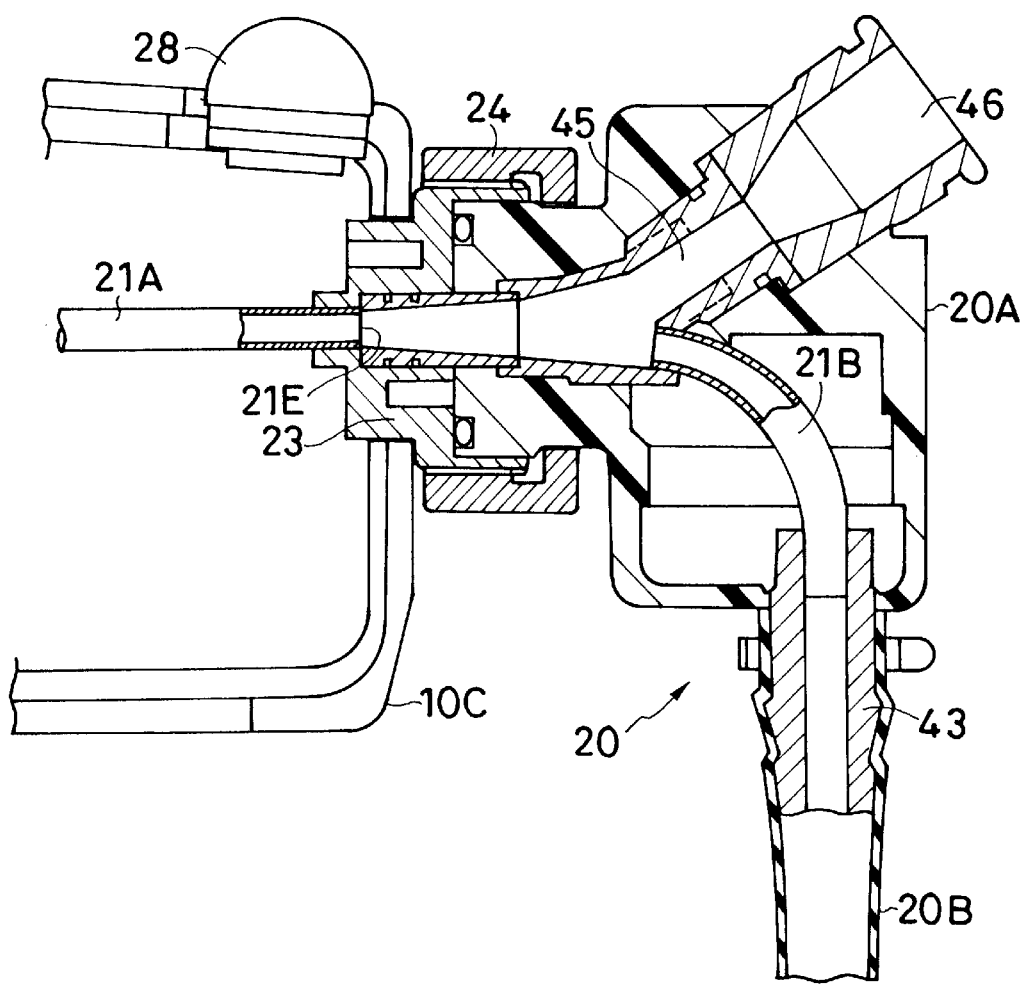
FIG. 5 shows the passage structure of the suction tube in the first embodiment, which is a sectional view of FIGS. 2(A) and 2(B) taken along the line III—III.
Figure 6:
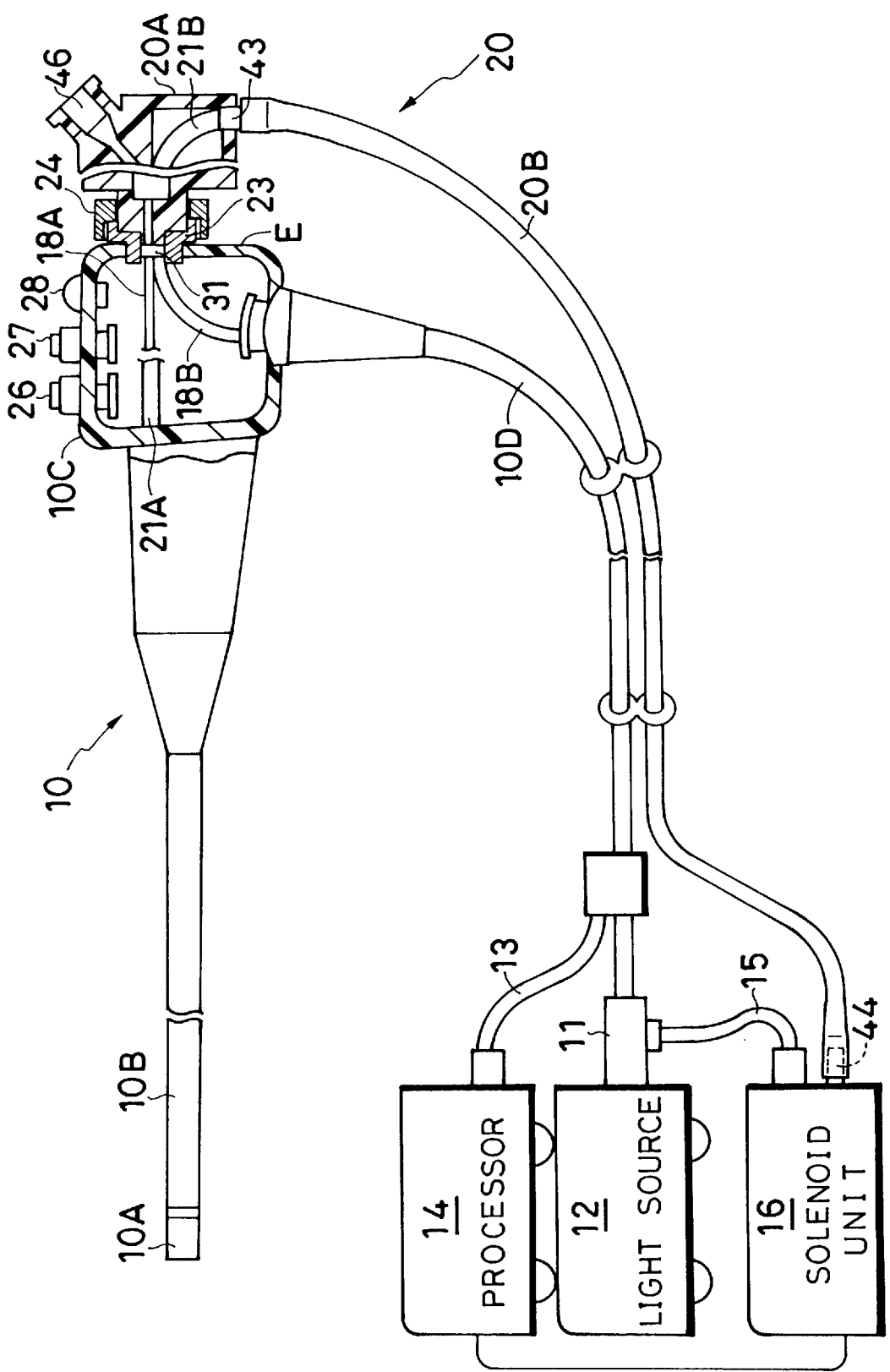
FIG. 6 shows the entire structure of the electronic endoscope in the first embodiment.

FIGS. 1 to 5 show a first embodiment of a passage structure in an endoscope according to the present invention, and FIG. 6 shows the entire structure of the endoscope. The entire structure of the endoscope will first be explained. In FIG. 6, the endoscope 10 is composed of an end portion 10A having a CCD, an insertion portion 10B, an operating portion 10C and a cable 10D. A connector 11 of the cable 10D connects the endoscope 10 to a light source 12, and a signal cable 13 connects it to a (image) processor 14. In the endoscope 10, light for irradiating a body cavity is supplied from the end portion 10A through a light guide disposed from the end portion 10a to the light source 12, and the CCD is controlled and a video signal is read through a signal line disposed from the end portion 10A to the processor 14.

A passage cable 15 branched from the cable 10D at the connector 11 is connected to a solenoid valve unit (operating value controller ) 16, and an air supply tube (not shown) and a water supply tube 18 are provided in the passage cable 15 and the cable 10D. The solenoid valve unit 16 is provided with a solenoid valve and the like for controlling a pump and a passage, as will be described later in detail, and it is electrically connected to the processor 14.

A passage unit 20 composed of a supporting portion 20A and a flexible suction tube 20B is removably provided in the operating portion 10C, and a suction tube 21A disposed in the operating portion 10C is connected with the flexible suction tube 20B. More specifically, a cylindrical receiving portion 23 with a male screw formed thereon is provided on the rear end surface of the operating portion 10C, and an operating ring 24 with a female screw formed on the internal periphery thereof is provided on the supporting portion 20A. The passage unit 20 is attached to the operating portion 10C by screwing the receiving portion 23 into the operating ring 24.

The supporting portion 20A of the passage unit 20 except for the passage portion which is formed of a metal tube is formed of a highly heat-resistant resin such as a polyethyleneimide resin which is free from thermal deformation so that it can be subjected to heat treatment for sterilization. A structure member such as a tube is not attached to the supporting portion 20A with an adhesive, but it is soldered thereto so as to maintain the heat resistance. The flexible suction tube 20B is formed of a soft synthetic resin material which has flexibility but which is not squashed by a suction pressure. Toaron tube (trade name) or the like is usable which is formed of such a soft synthetic resin material reinforced by winding a tight coil therearound in order to prevent the tube from being squashed.

Figure 1:
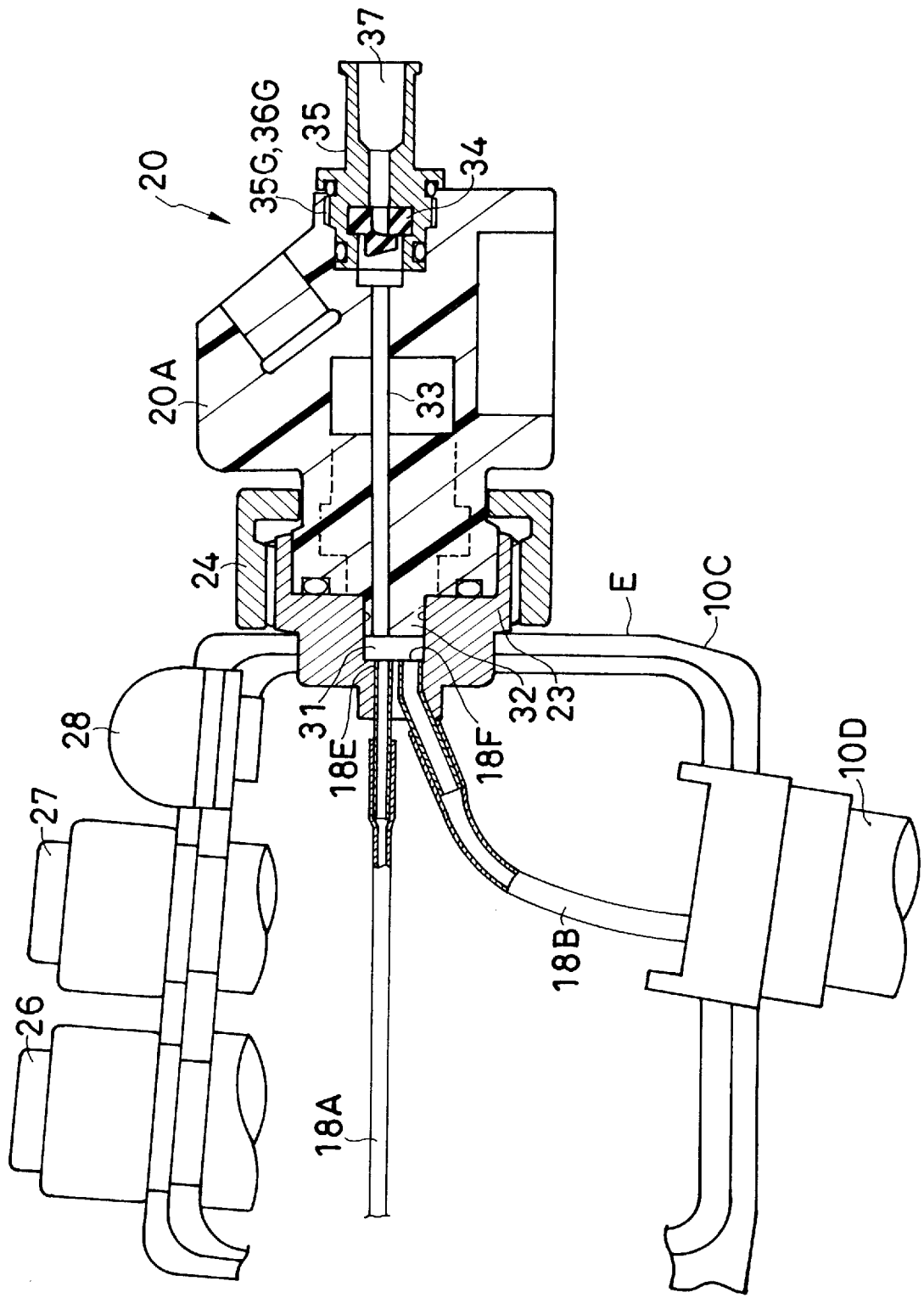
FIG. 1 shows a first embodiment of a passage structure (water supply tube) in an endoscope according to the present invention, which is a sectional view of FIGS. 2(A) and 2(B) taken along the line I—I.
Figure 2:
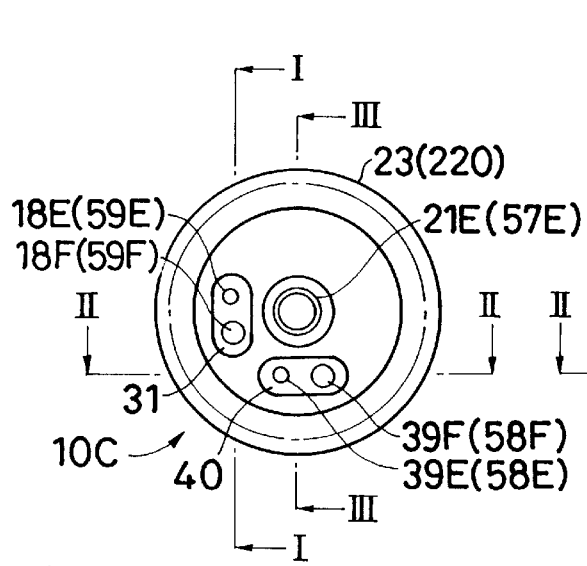
FIG. 2(A) shows the structure of the coupling portion of the operating portion which is separated from the passage unit in each embodiment.
FIG. 2(B) shows the structure of the coupling portion of the passage unit which is separated from the operating portion in each embodiment.
Figure 2:
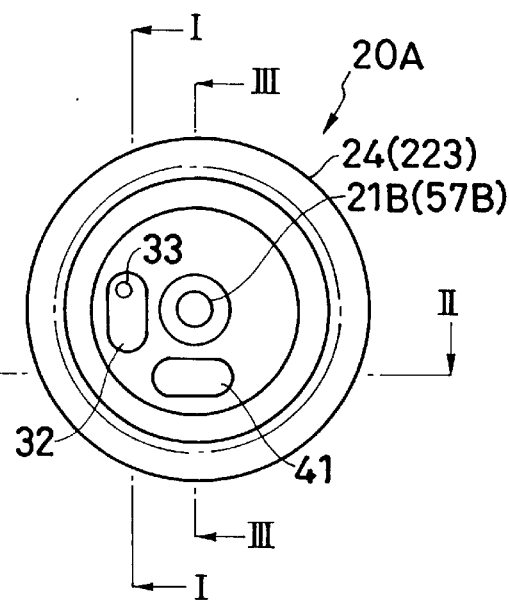

As shown in FIG. 1, the operating portion 10C is provided with a air supply/water supply switch (two-staged switch) 26, a suction switch 27 and a photographing button 28, which are electrical switches, and operation control signals for these switches are transmitted to the solenoid valve unit 16. In other words, a pinch valve or the like in the solenoid valve unit 16 is opened or closed in accordance with an electrical operation control signal so as to control the flow in a passage.

FIG. 1 is a sectional view of FIGS. 2(A) and 2(B) taken along the line I—I and shows the structure of the water supply tube 18. In the operating portion 10c, a forward water supply tube 18A which is disposed from the forward end toward the rear end surface is separated from a rear water supply tube 18B disposed from the rear end surface toward the cable 10D. A return portion 31 constituted by a predetermined passage space is formed in the receiving portion 23, and the openings 18E and 18F of the forward and rear water supply tubes 18A, 18B, respectively, are disposed in the return portion 31. The return portion 31 may be formed in the passage unit 20.

The supporting portion 20A into which the receiving portion 23 is fitted is provided with a plug member 32 such as a packing in a convex shape which is fitted into a part of the return portion 31a, and an auxiliary tube 33 is laid from the plug member 32 toward the rear end portion of the supporting portion 20A. An injection hole member 35 provided with a check valve 34 is removably attached to the supporting portion 20A in connection with the auxiliary tube 33.

Figure 3:
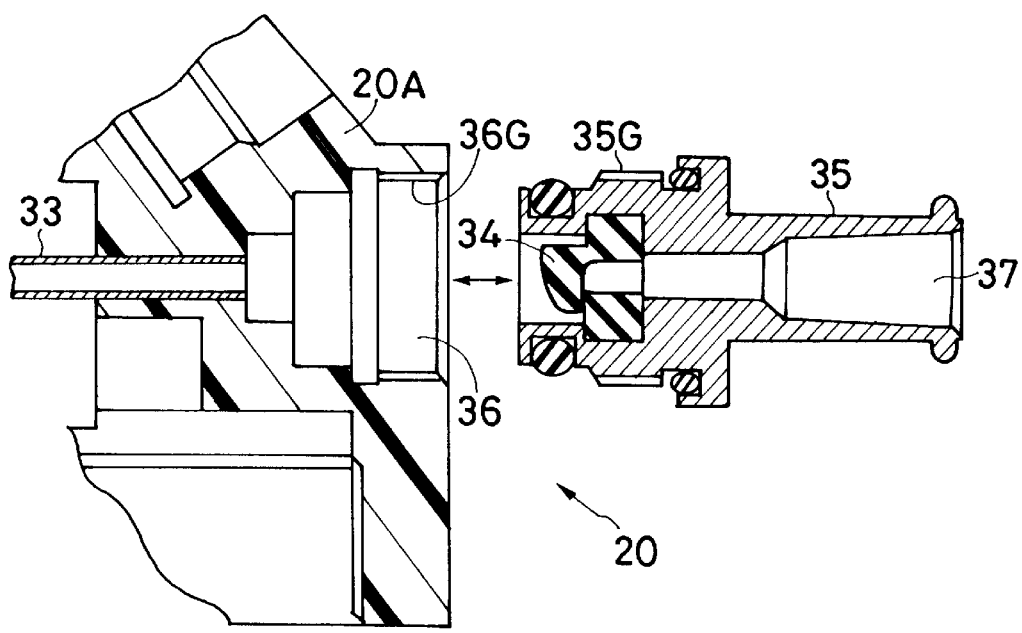
FIG. 3 is an enlarged view of the injection hole member of the supporting portion shown in FIG. 1.

As shown in the enlarged view of FIG. 3, in the supporting portion 20A, a female screw 36G is formed in a fitting portion 36 which is connected to the auxiliary tube 33, and a male screw 35G to be engaged with the female screw 36G is formed on the injection hole member 35. Owing to the screws 35G and 36G, the injection hole member 35 is freely attached to and removed from the supporting portion 20A. An O-ring is placed over the injection hole member 35 so as to maintain the airtightness. A lens surface washing water injection hole 37 is provided in the injection hole member 35. It is possible to freely attach and remove the check valve 34 to and from the opening at the forward end of the injection hole member 35.

According to the injection hole member 35, it is possible to wash the observation window of the end portion 10A of the endoscope during use by supplying water or the like from the lens surface washing water injection hole 37 by an injection syringe or the like. It is also possible to remove the injection hole member 35 from the supporting portion 20A so as to replace the check valve 34 with a new one after the endoscope 10 is used.

FIG. 4 is a sectional view of FIGS. 2(A) and 2(B) taken along the line II—II, and shows the structure of an air supply tube. In this case, the air supply tube is also divided into a forward air supply tube 39A and a rear air supply tube 39B, and the respective openings 39E, 39F are disposed in a return portion 40. A plug member 41 which is fitted into the return portion while securing a flow returning space is disposed in the supporting portion 20A.

FIG. 5 is a sectional view of FIGS. 2(A) and 2(B) taken along the line III—III and shows the passage structure of the suction tubes 21A, 21B. In this embodiment, the suction tubes 21A, 21B are disposed in different passages. More specifically, the forward suction tube 21A is provided in the operating portion 10C, and the opening 21E thereof is disposed at the center portion of the receiving portion 23, while the rear suction tube 21B is disposed in the passage unit 20. In the supporting portion 20A of the passage unit 20, a connecting tube 43 is attached to the rear suction tube 21B, as shown in FIG. 5, and the connecting tube 21B is inserted into one end of the flexible suction tube 20B of, for example, a soft synthetic resin material. The other end of the flexible suction tube 20B is fitted over a connecting tube (similar to the connecting tube 43) disposed at the solenoid valve unit 16, as shown in FIG. 6.

The supporting portion 20A is provided with a forceps hole 46 through a branched tube 45 which is branched from the suction tube 21B, and a cap (not shown) as a plug is filled into the forceps hole 46. Thus, the suction tubes 21A, 21B not only suck water or the like within the body as an object of observation, but also function as treatment tool insertion channels.

In the first embodiment having the above-described structure, when the endoscope 10 is used, the passage unit 20 is connected to the operating portion 10C by connecting the operating ring 24 to the receiving portion 23. In this state, air supply/water supply operation and suction operation are enabled on the basis of the operation of the air supply/water supply switch (two-staged switch) 26 and the suction switch 27. That is, when the operation control signals of the switches 26, 27 are transmitted to the solenoid valve unit 16 through the processor 14 shown in FIG. 6, the control circuit in the solenoid valve unit 16 operates the pump and opens or closes the corresponding solenoid valve.

In the case of air supply/water supply operation, air is supplied to the end portion 10A through the rear air supply tube 39B, the return portion 40 and the forward air supply tube 39A (FIG. 4), or water is supplied to the end portion 10A through the rear water supply tube 18B, the return portion 31 and the forward water supply tube 18A (FIG. 1). It is also possible to wash the observation lens during the use of the endoscope 10 by supplying injection water, for example, from the lens surface washing water injection hole 37 of the passage unit 20 by an injection syringe or the like. In the case of sucking operation, the contaminated water or the like in the body being observed is sucked through the suction tubes 21A, 21B and the flexible suction tube 20B. If a treatment tool is inserted into these suction tubes 21A, 21B from the forceps insertion hole 46, various treatments are possible.

Figure 7:
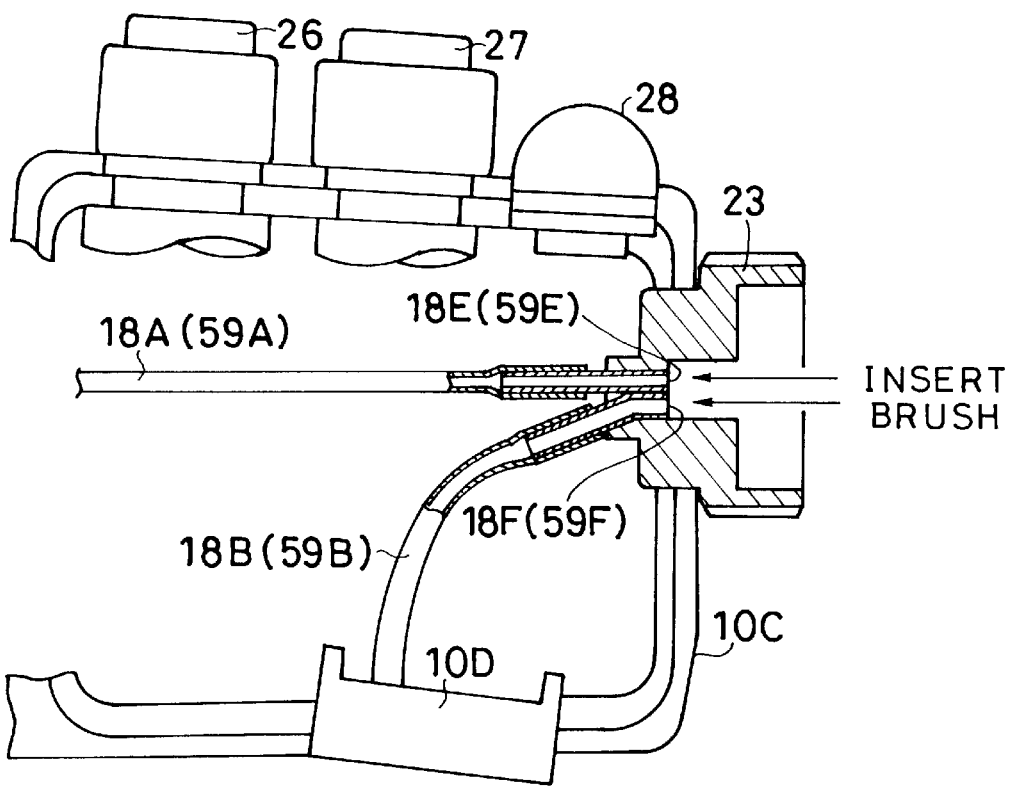
FIG. 7 shows the passage unit shown in FIG. 1 in the state of being removed from the operating portion.

When the passages are washed and sterilized after the endoscope 10 is used, the passage unit 20 is removed from the operating portion 10C in the state shown in FIG. 7, and it is possible to insert a washing brush from the rear end portion of the operating portion 10C. In this case, it is possible to wash all the passages in the endoscope 10 by successively inserting the washing brush from the openings 18E, 18F of the water supply tubes 18A, 18B, from the openings 39E, 39F of the air supply tubes 39A, 39B, and from the opening 21E of the suction tube 21A, as shown in FIG. 2(A). That is, in this embodiment, since the openings for receiving the washing brush are collectively disposed at one place, the conventional complicated setting of a washing device or the attachment of an adapter is dispensed with, thereby enhancing the washing efficiency.

In the passage unit 20, the injection hole member 35 is separated from the supporting portion 20A, and the check valve 34 contaminated with various germs is removed, as shown in FIG. 3. The flexible suction tube 20B is also removed from the connecting tube 43, as shown in FIG. 5. In this state, the auxiliary tube 33 and the suction tube 21B are washed with a washing brush. Thereafter, the passage unit 20 is subjected to sterilization (heat disinfection) in an autoclave or the like, and the check valve 34 and the flexible suction tube 20B are replaced with new ones. That is, according to this embodiment, it is advantageously possible to keep the passages in the endoscope clean by washing only the supporting portion 20A of the passage unit 20 and subjecting the supporting portion 20A to sterilization in an autoclave or the like.

In the above explanation, the auxiliary tube 33 is used when flushing the lens surface. In some endoscopes, however, an injection hole for supplying air/water to the interior of the body being observed is provided at the end portion as a jet hole or the like, and a passage to the injection hole is provided separately from the air/water supply tube used when injecting air/water to the observation window. It is possible to connect the auxiliary tube with such a passage of the jet hole. In this case, a jet water injection hole is provided in the injection hole member 35.

Figure 8:
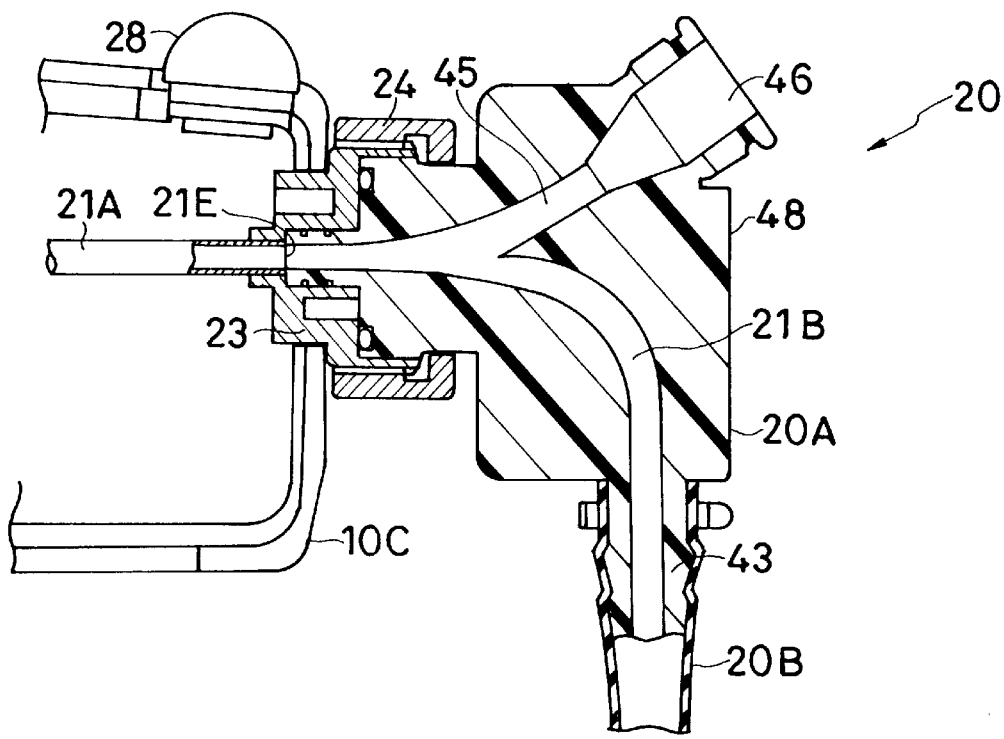
FIG. 8 shows another structure of the supporting portion of the passage unit in the first embodiment.

In the example shown in FIG. 8, the passage unit 20 as a whole is made disposable. In the above explanation, the supporting portion 48 of the passage unit 20 is formed of a polyethyleneimide resin which can be subjected to heat treatment. In contrast, in the example shown in FIG. 8, the supporting portion 48 is formed of an inexpensive hard synthetic resin material, passages are integrally formed within the supporting portion 48 without using a metal tube, and the flexible tube 20B is connected to the connecting tube 43 of the supporting portion 48. According to this structure, it is possible to use the passage unit 20 as a whole including the supporting portion 48 only once and then throw it away. As a result, the washing and disinfection of the passage unit 20 as a whole are unnecessary.

As explained above, according to the first embodiment, since the passages are exposed to the return portion in the operating portion, the passage unit is removably attached to the operating portion, and the injection hole member is removably attached to the auxiliary tube provided in the passage unit so as to enable the replacement of the disposable check valve, it is possible to wash all the passages in the operating portion with a washing brush and to facilitate washing operation owing to the disposable check valve.

In addition, it is possible to sterilize the passage unit. Furthermore, if the passage unit as a whole is made disposable, it is unnecessary to wash or sterilize the passage unit.

Second embodiment

Figure 9:
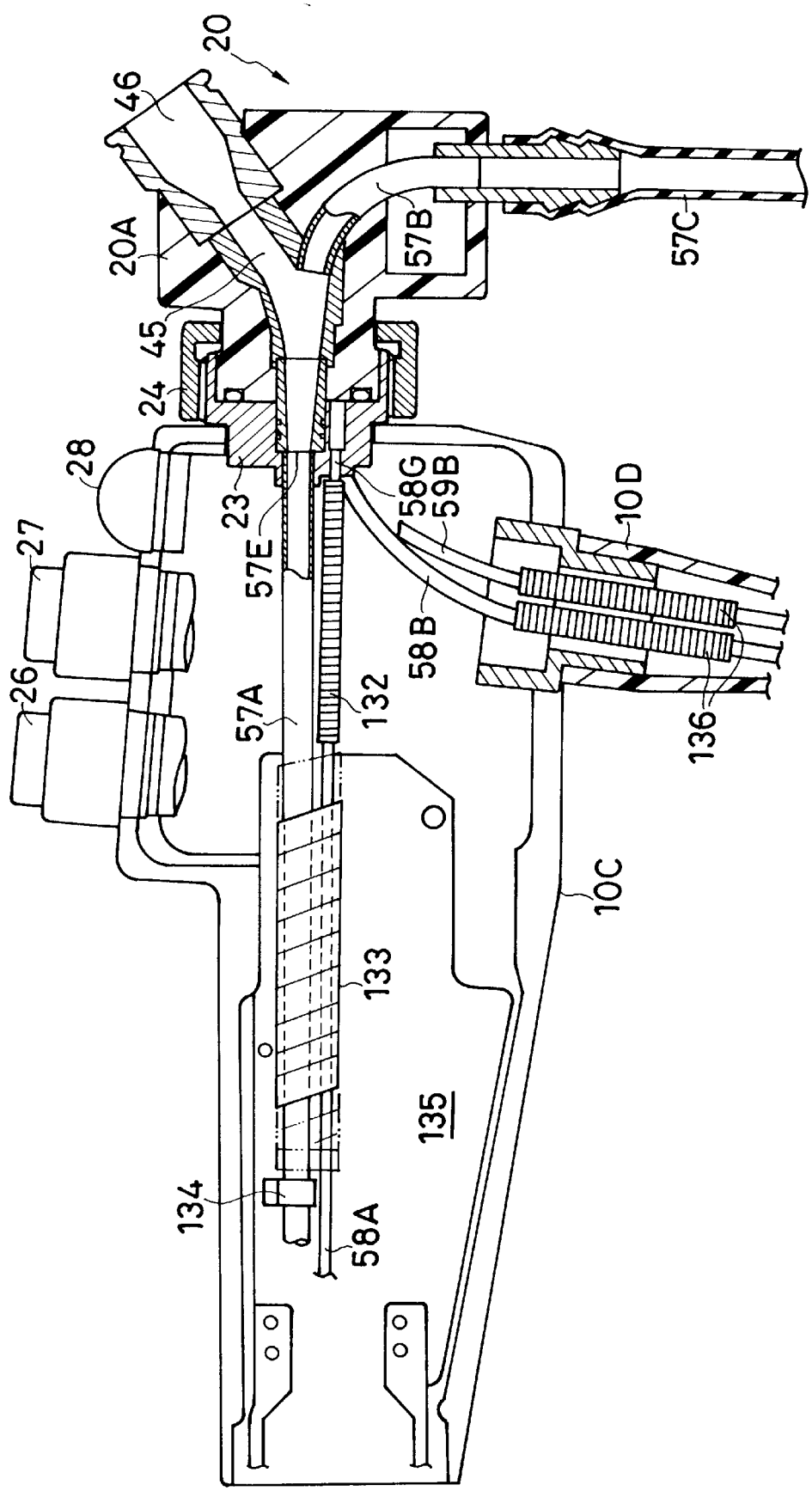
FIG. 9 shows a second embodiment of a passage structure in an endoscope according to the present invention, which is a sectional view of FIGS. 2(A) and 2(B) taken along the line III—III.
Figure 10:
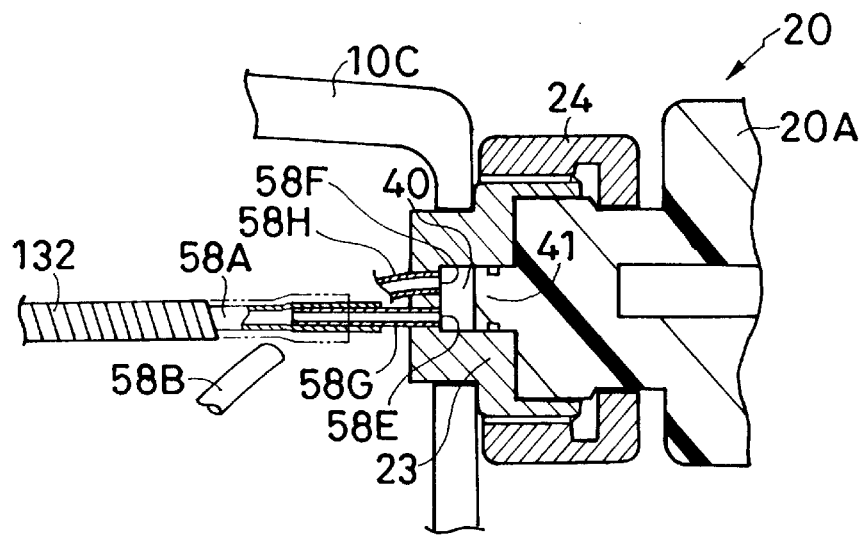
FIG. 10 shows the passage structure of the air supply tube in the second embodiment, which is a sectional view of FIGS. 2(A) and 2(B) taken along the line II—II.
Figure 11:
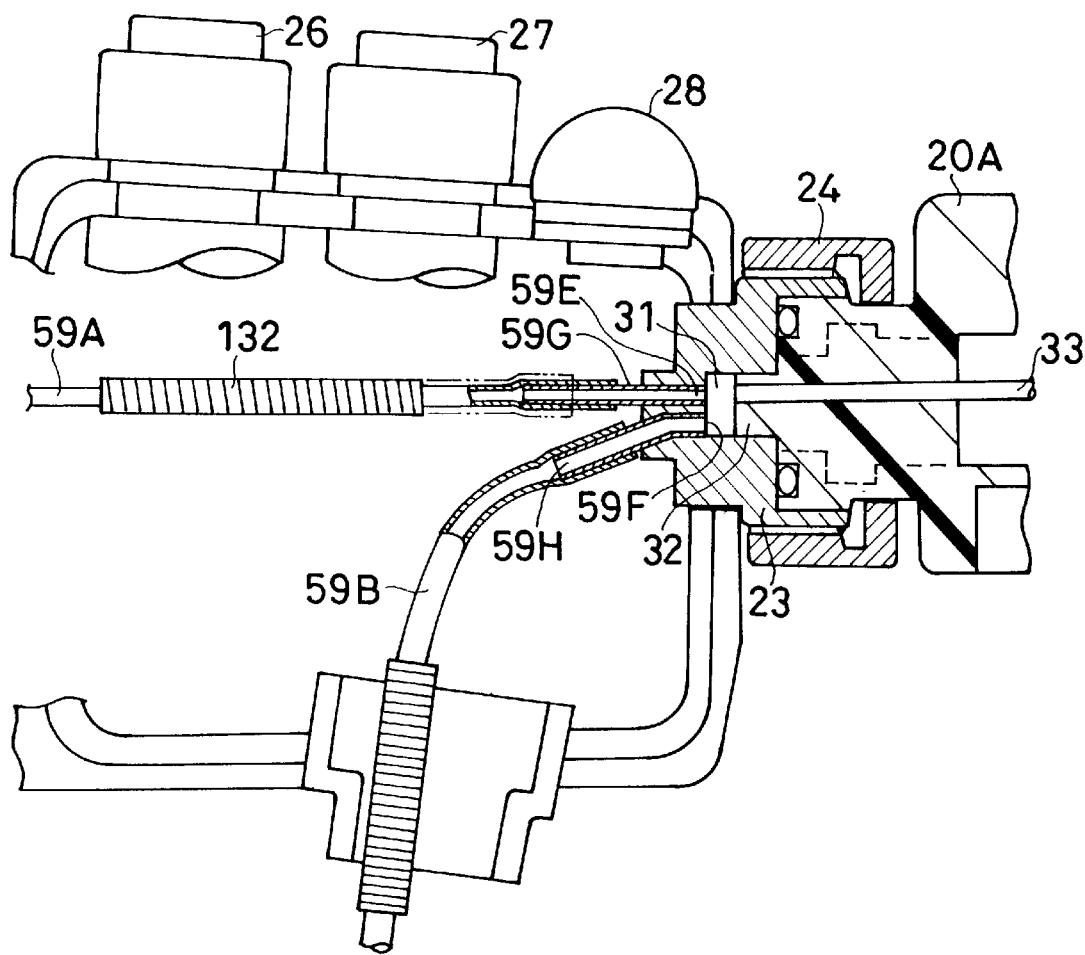
FIG. 11 shows the passage structure of a water supply tube in each embodiment, which is a sectional view of FIGS. 2(A) and 2(B) taken along the line I—I.

FIGS. 9 to 11 show a second embodiment of a passage structure of an endoscope. In the second embodiment, a passage is prevented from being bent or warped with a brush inserted thereinto. For example, referring to the water supply tubes 18A, 18B shown in FIG. 7, soft tubes are used for these tubes except for the connecting portion or the like, so that during the washing of the interior of the tube, the passage is bent or warped inconveniently for washing. If the washing brush applies strong force to the tube, the soft tube may sometimes slip out of the connecting portion or may even be broken. This is the same with an air supply tube and the like. To prevent this, a tight spring or the like is fitted over the soft tube in the second embodiment.

In FIG. 9, the main structure of the second embodiment is the same as that of the first embodiment. The operating portion 10C is provided therewithin with a suction tube 57A made of a hard tube such as a metal tube, air supply tubes 58A, 58B, and water supply tubes 59A (FIG. 11), 59B each of which is formed of a soft tube except for the connecting portion. These passages 57A to 59B are laid so as to reach the receiving portion as a connector at the rear end of the operating portion 10C. Each of the forward suction tube 57A, the air supply tube 58A and the water supply tube 59A is disposed in a straight line at least within the operating portion 10C. The operating portion 10C is provided with the passage unit 20 in the same way as in the first embodiment in order to form a return portion of the air supply tubes 58A, 58B and the water supply tubes 59A, 59B and in order to connect a suction tube 57B to the suction tube 57A.

More specifically, the passage unit 20 is attached to the operating portion 10C by screwing the receiving portion 23 having a male screw into the operating ring 24 having a female screw fitted on the supporting portion 20A. The passage unit 20 is provided with the suction tube 57B which is to be connected to the suction tube 57A, and a flexible suction tube 57C which is removably attached to the supporting portion 20A. The passage unit 20 is also provided with the forceps hole 46 or the like which function as a treatment tool insertion channel for introducing a treatment tool.

FIG. 10 shows the structure of the air supply tube 58. A return portion 40 for securing a flow returning space is formed in the receiving portion 23, and the openings 58E and 58F of the forward and rear water supply tubes 58A, 58B, respectively, are disposed in the return portion 40. The supporting portion 20A holding the operating ring 24 is provided with a convex plug member 41 which is fitted into a part of the return portion 40. In this manner, when the passage unit 20 is attached to the operating portion 10C, the return portion 40 having a predetermines space is formed, which enables air to be supplied from the rear air supply tube 58B to the forward air supply tube 58A.

FIG. 11 shows the structure of the water supply tube 59. This structure is also the same as that in the first embodiment. A return portion 31 having a predetermined passage space is formed in the connecting portion, and water is suppled from the rear water supply tube 59B to the end portion through the return portion 31 and the forward water supply tube 59A. It is also possible to supply injection water to the end portion through the injection hole, the auxiliary tube 33 and the forward water supply tube 59A by using an injection syringe or the like.

Among these passages in the endoscope, a tight spring 132 is fitted over the forward supply air tube 58A and the forward water supply tube 59A at the portions of the soft tubes disposed in straight lines, as shown in FIGS. 10 and 11, respectively. This will be explained with reference to the air supply tube 58 shown in FIG. 10 as an example. The soft air supply tube 58A is connected to a metal connecting tube 58G, and the tight spring 132 is fitted over a part of the air supply tube 58A and a part of the connecting tube 58G. The diameter of the tight spring 132 is so set as to enable the tight spring 132 to be fixed around the connecting tube 58G by clamping. For example, the tight spring 132 has an inner diameter slightly smaller than the outer diameter of the air supply tube 58A, and it is soldered to the end portion. This is the same with the water supply tube 59A shown in FIG. 11.

The air supply tube 58A and the water supply tube 59A are laid along the suction tube 57A which is a hard tube, and the portions of the three tubes which are not covered with the tight spring 132 are bundled together with a tape 133 so as to be fixed, as shown in FIG. 9. In this case, the suction tube 57A is fixed and secured to a support board 135 by a fixing metal 134.

In this embodiment, as shown in FIG. 9, a tight spring 136 is placed over the straight portions of the rear air supply tube 58B and the rear water supply tube 59B disposed in the connecting portion of the cable 10D. The tight spring 136 is also fixed in such a manner as not to move within the cable 10D.

In the second embodiment having the above-described structure, when the passages are washed and sterilized after the endoscope 10 is used, the passage unit 20 is removed from the operating portion 10C in the state shown in FIG. 2(A) or 7, and it is possible to insert a washing brush from each of the openings 57E, 58E, 58F, 59E and 59F in the receiving portion 23. At this time, although there is no problem in the suction tube 57A which is a hard tube, there is a possibility of the soft portions of other tubes 58A to 59B being bent or warped by the washing brush in a conventional device.

In this embodiment, however, since the tight spring 132 is provided and the forward air supply tube 58A and water supply tube 59A are bundled with the tape 133 along the suction tube 57A, the soft portions of the forward air supply tube 58A and the forward water supply tube 59A are maintained in a straight line free from bending and warping. Although there are partially bent soft portions between connecting tubes 58H, 59H of the receiving portion 23 and the straight portions, since these portions are short and the straight portions of the tubes 58B and 59B in the cable 10D are maintained to be straight owing to the tight spring 136, it is possible to prevent these portions from being bent or warped.

In the second embodiment, the passages within the operating portion 10C are covered with the tight spring 132 and also bundled with the tape 133. It is preferable to appropriately apply this measure to other parts, as occasion demands. In the endoscope inserting portion and the cable 10D, however, passages and various elements are arranged without a space, there may be no positive necessity.

Although the tight spring 132 and the tape 133 are used in combination in the above example, it is possible to use only the tight spring 132 which is fitted over the appropriate soft tubes in the operating portion 10C. Furthermore, it is also possible to make all the passages within the operating portion 10C of a hard tube in the same way as the suction tube 57A.

Third embodiment

Figure 12:
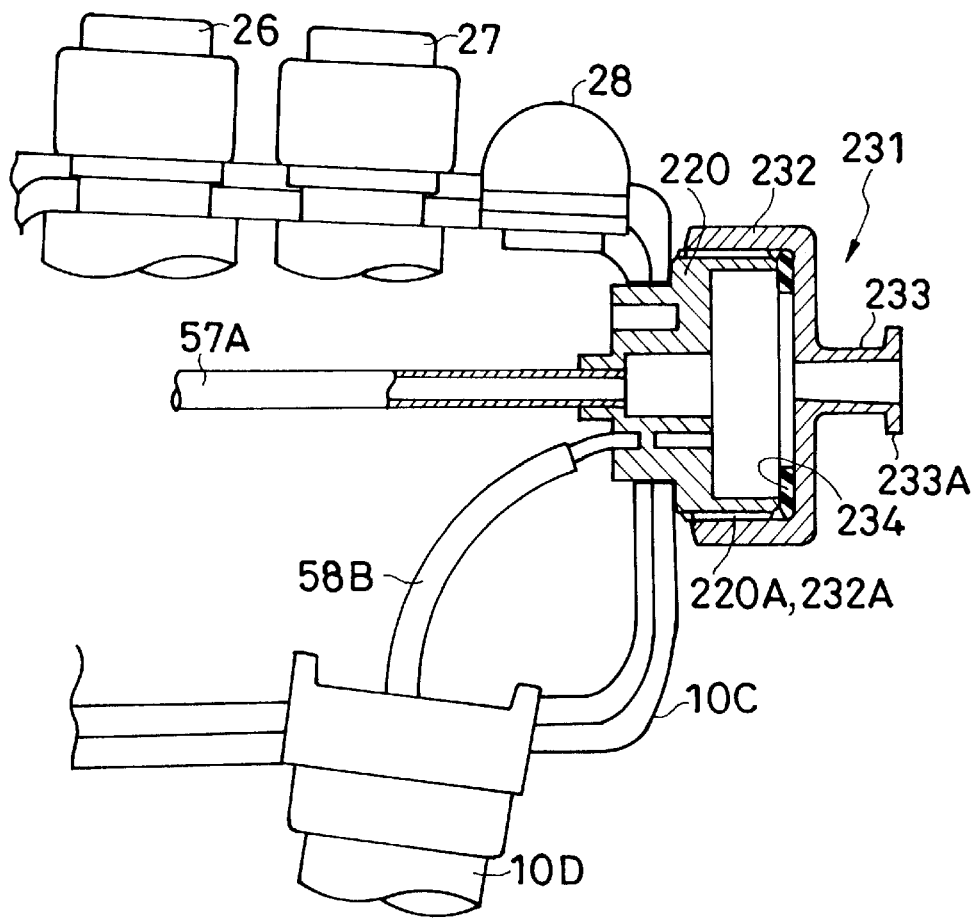
FIG. 12 is a sectional view of a third embodiment of a passage structure in an endoscope according to the present invention, in a state in which an adapter used when washing passages is attached to the openings of the passages of the operating portion.

FIGS. 12 to 16 show a third embodiment of a passage structure of an endoscope. In the third embodiment, an adapter is used when washing the passages in the endoscope having the same structure as those in the first and second embodiment. In FIG. 12, various tubes such as the forward suction tube 57A and the rear air supply tube 58B are disposed in the operating portion 10C and the opening of these passages are connected to a receiving portion 220 (first coupling portion). As shown in FIG. 2(A), the receiving portion 220 is provided with the openings (57E, 58E, 58F, 59E and 59F) of the forward (near the end portion) suction tube 57A, the forward air supply tube 58A, the rear air supply tube 58B, the rear (near the solenoid unit) water supply tube 58B, the forward water supply tube 59A and the rear water supply tube 59B, respectively.

Figure 14:
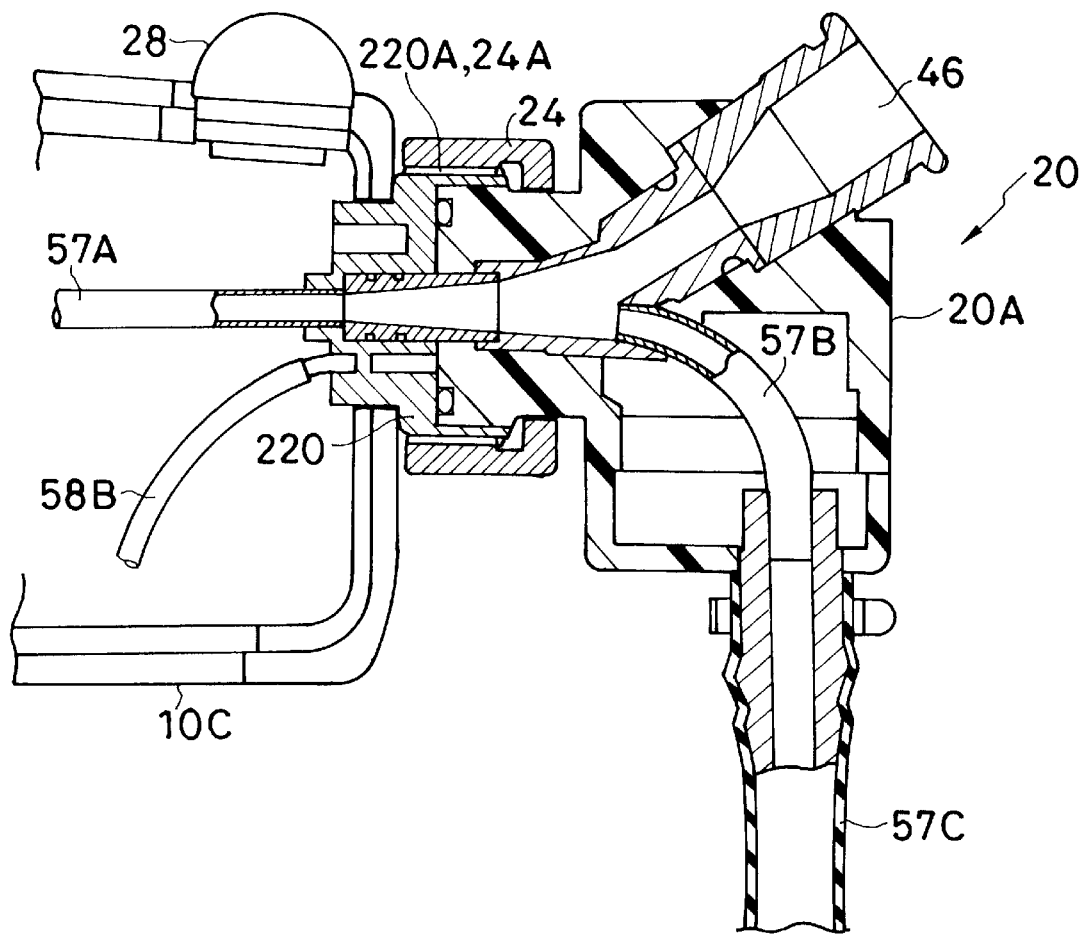
FIG. 14 is a sectional view of the passage unit in the third embodiment which is attached to the operating portion of the endoscope shown in FIG. 1, the passage being a sectional view of FIGS. 2(A) and 2(B) taken along the line III—III.
Figure 15:
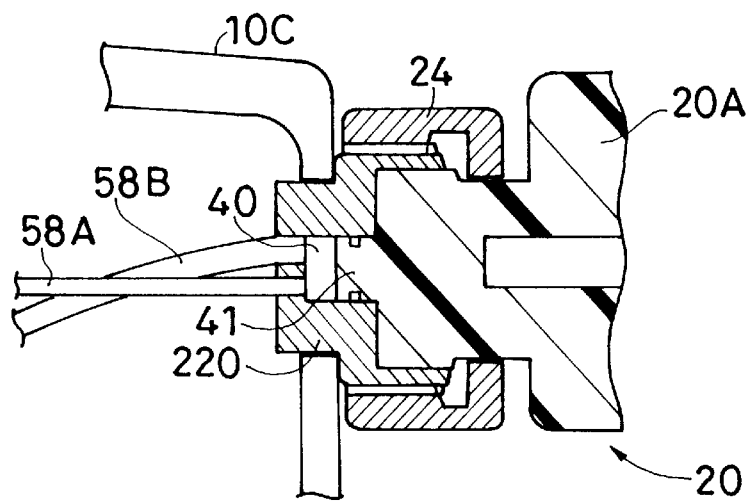
FIG. 15 shows the passage structure of the air supply tube in the third embodiment, which is a sectional view of FIGS. 2(A) and 2(B) taken along the line II—II.

FIG. 14 shows the passage unit 20 attached to the operating portion 10C shown in FIG. 12. The operating ring (fixing ring) 24 of the supporting portion 20A as a second coupling portion is removably attached to the receiving portion 220 as the first coupling portion. As shown in FIG. 15, the air supply tubes 58A and 58B are connected with each other through the return portion 40, while the water supply tubes 59A and 59B are connected with each other through the return portion 31, as shown in FIG. 16.

Figure 13:
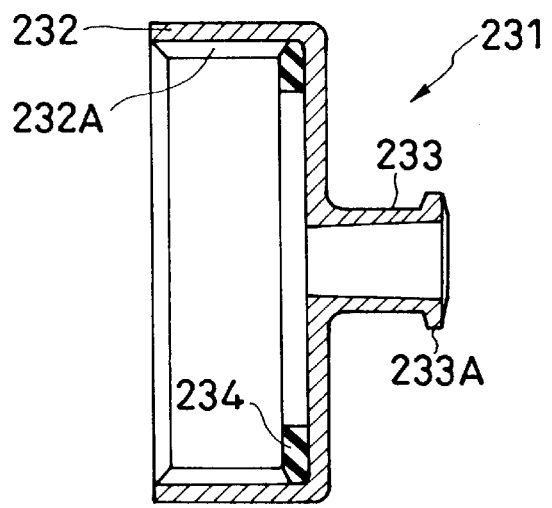
FIG. 13 is a sectional view of the adapter used when washing passages in the endoscope in the third embodiment.

An adapter 231 used when washing passages is removably attached to the receiving portion 220 of the operating portion 10C, as shown in FIG. 12. The adapter 231 is composed of a third coupling portion 232 having a shape of a cap with a female screw 232A formed on the inner periphery, and a washing water injection hole 233 for receiving the point of an injection syringe or a liquid chemical injector, as shown in FIG. 13. The receiving portion 220 is provided with a male screw 220A on the outer periphery thereof which can be screwed into the third coupling portion 232. A rubber packing 234 is provided on the inside of the third coupling portion 232 so as to maintain the airtightness at the time of coupling. At the end portion of the injection hole 233, an annular projecting portion 233A is provided, and the annular projecting portion 233A can be screwed into, for example, an injector fixing member 236A with a female screw formed on the inside thereof, as shown in FIG. 16.

In the third embodiment having the above-described structure, when the endoscope 10 is used, the passage unit 20 is connected to the operating portion 10C by connecting the operating ring 24 as the second coupling portion to the receiving portion 220, as shown in FIG. 14. In this state, air supply/water supply operation and suction portion are enabled on the basis of the operation of the air supply/water supply switch 26 and the suction switch 27. That is, the solenoid valve unit 16 operates the pump and opens or closes the corresponding solenoid valve. In the case of sucking operation, the contaminated water or the like in the body being observed is sucked through the suction tubes 57A, 57B and the flexible suction tube 57C. In the case of air supply operation, air is supplied through the rear air supply tube 58B, the return portion 40 and the forward air supply tube 58A, as shown in FIG. 15, and in the case of water supply, water is similarly supplied through the rear water supply tube 59B, the return portion 31 and the forward water supply tube 59A (see FIG. 16).

Figure 16:
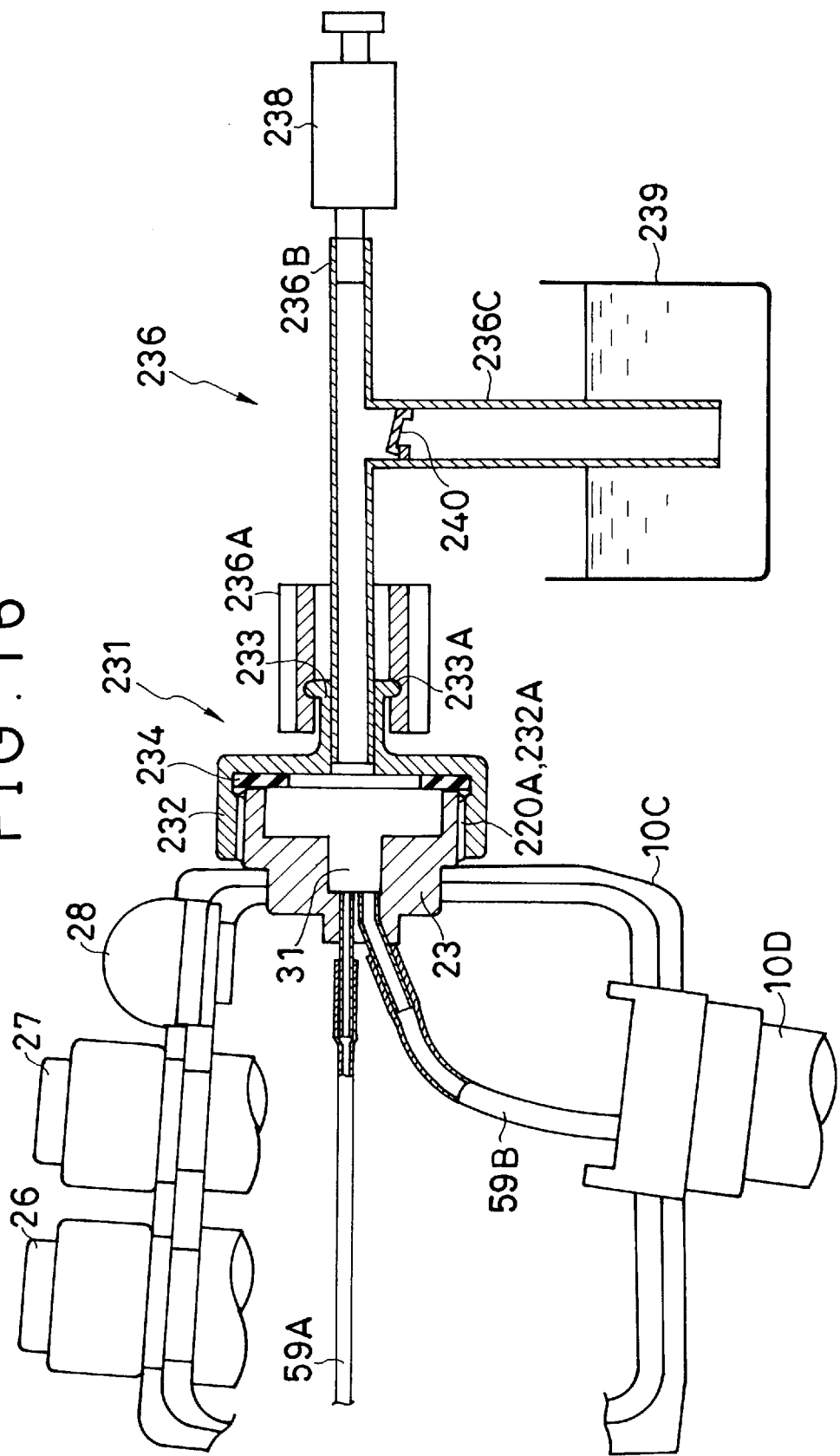
FIG. 16 shows the structure of the third embodiment when a liquid chemical is supplied, the passage being a sectional view of FIGS. 2(A) and 2(B) taken along the line I—I.

When the passages are washed and sterilized after the endoscope 10 is used, the passage unit 20 is removed from the operating portion 10C, and the adapter 231 is attached to the receiving portion 220, as shown in FIG. 12 or 16. That is, the male screw 220A of the receiving portion 220 as the first coupling portion is engaged with the female screw 232A of the third coupling portion 232, and the airtightness of the coupling portion is maintained by the rubber packing 234 provided in the third coupling portion 232. The point of an injection syringe may be directly inserted into the injection hole 233 of the adapter 231. Alternatively, an injector 236 shown in FIG. 16 may be adopted for washing.

The injector 236 is composed of the above-described fixing member 236A, a guide hole 236B for the injector 236, a passage 236C for sucking a liquid chemical from a liquid chemical tank 239, a check valve 240 disposed in the passage 236C, and the like. The fixing member 236A of the injector 236 is fixed on the injection hole 233 (annular projecting portion 33A) of the adapter 231 by screwing. The liquid chemical sucked from the liquid chemical tank 239 is supplied to each passage from the injection hole 233 through the receiving portion 220 by the piston motion of an injection syringe 238. Although only the water supply tubes 59A, 59B are shown in FIG. 16, the liquid chemical is also supplied to all the passages of the suction tube 57A, and the air supply tubes 58A, 58B, and each passage is washed.

In the above example, the first coupling portion (receiving portion 220), the second coupling portion (operating ring 24) and the third coupling portion 232 are coupled by screwing. But coupling means is not limited to screwing. For example, a pin may be disposed on the outer periphery of the receiving portion 220, and a guide groove which is inclined forward and backward may be provided on the operating ring 24. When the first coupling portion is coupled with the second coupling portion, the pin is engaged with the guide groove. That is, a coupling structure for fixing the coupled state by rotating the operating ring 24 and engaging the guide groove with the pin may be adopted.

It is possible to reverse the coupling relationship, and the receiving portion 220 may be provided in the passage unit 20, while the operating ring 24 and the third coupling portion 232 are provided in the operating portion 10C.

As described above. according to the third embodiment, it is possible to easily supply a liquid chemical even to fine passages which are separated in the middle of a passage or which have different diameters. In addition, since the suction tube, air/water supply tubes are collectively disposed in the first coupling portion, it is possible to supply washing water to all of these passages at one time.

While there has been described what are at present considered to be preferred embodiments of the invention, it will be understood that various modifications may be made thereto, and it is intended that the appended claims cover all such modifications as fall within the true spirit and scope of the invention.

What is claimed is:

1. A passage structure of an endoscope comprising:
    an operating portion which is provided therein with passages of said endoscope;
    a passage unit which is removably attached to said operating portion and which is provided with a passage for connecting said passages in said operating portion to an operating valve controller;
    a return portion for separating at least one of said passages so that the openings thereof are exposed to the outer peripheral portion of said operating portion, and forming a flow returning space at the exposed portions of said openings when said passage unit is mounted on said operating portion;
    an auxiliary passage provided in said operating portion in such a manner as to be connected to said return portion; and
    an injection hole member removably attached to said passage unit and provided with a check valve which is replaceable when said injection hole member is removed from said passage unit.

2. A passage structure of an endoscope according to claim 1, wherein said passage unit includes a supporting portion formed of a highly heat-resistant synthetic resin material which can be subjected to heat disinfection, and a flexible tube which is disposed from said supporting portion to said operating valve controller in such a manner as to be removably attached to connecting tubes of said supporting portion and said operating valve controller.

3. A passage structure of an endoscope according to claim 1, wherein said passage unit is disposable and includes a supporting portion of a synthetic resin material within which a passage is integrally formed, and a flexible tube connected to said supporting portion.

4. A passage structure of an endoscope comprising:
    an operating portion which is provided therein with passages of said endoscope;
    a passage unit which is removably attached to said operating portion and which is provided with a passage for connecting said passages in said operating portion to an operating valve controller; and
    a return portion for separating at least one of said passages so that the openings thereof are exposed to the outer peripheral portion of said operating portion, and forming a flow returning space at the exposed portions of said openings when said passage unit is mounted on said operating portion;
    wherein when said passages include a soft tube disposed in a straight line, a tight spring is fitted over said soft tube.

5. A passage structure of an endoscope according to claim 4, wherein said passages further include a hard tube, and said soft tube and said hard tube are bundled in a state in which said soft tube is placed along said hard tube.

6. A passage structure of an endoscope according to claim 4, wherein said hard tube is a suction tube, and said soft tube is either of an air supply tube and a water supply tube.

7. An adapter used when washing passages in an endoscope which is provided with a main body having a first coupling portion where the openings of said passages in said main body are disposed, and a passage unit having a second coupling portion to be coupled with said first coupling portion and maintaining the passage function, said adapter comprising:

a third coupling portion which is coupled with said first coupling portion in such a manner that the space communicating with said openings of said passages is in an airtight state; and a washing water injection hole which is connected to said space communicating with said openings of said passages.

8. An adapter used when washing passages in an endoscope according to claim 7, wherein said passages with said openings disposed in said first coupling portion are a suction tube, an air supply tube and a water supply tube, and washing water is supplied from said washing water injection hole to all of said passages.

* * * * *